Nov. 18, 1947. E. H. CARTER Plant Pat. 766
CAMELLIA PLANT
Filed March 24, 1947
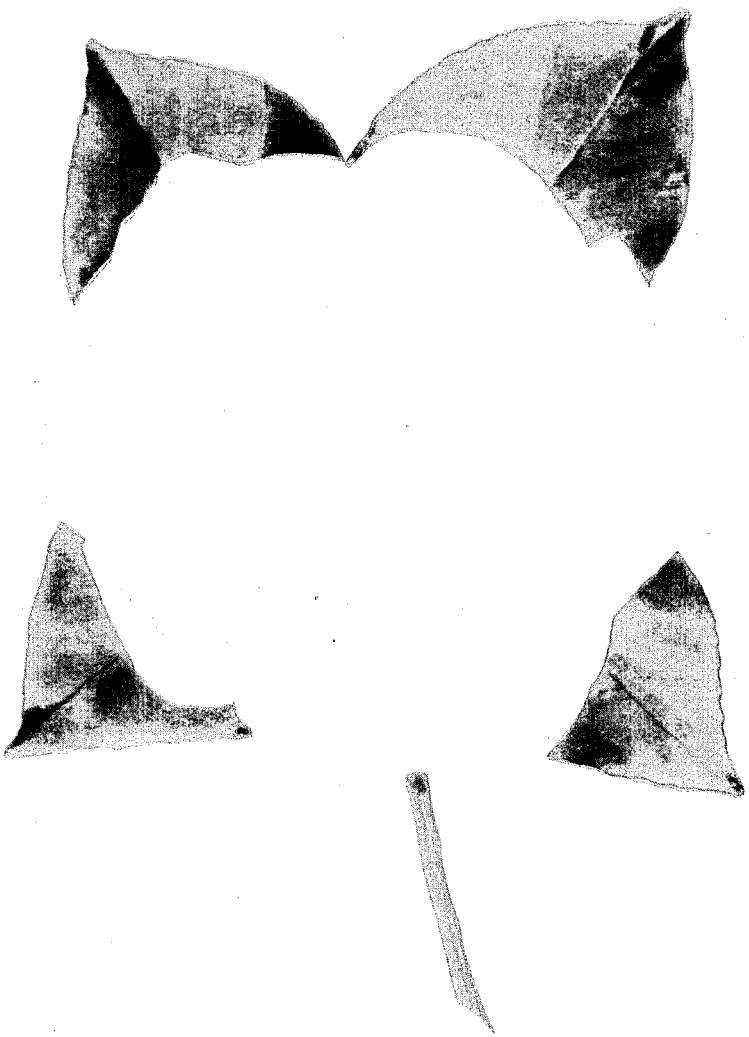
Inventor
E. H. Carter
By Robb & Robb
Attorneys Patented Nov. 18, 1947

Plant Pat. 766

UNITED STATES PATENT OFFICE

766

CAMELLIA PLANT

Elvin H. Carter, Monterey Park, Calif.

Application March 24, 1947, Serial No. 736,793

1 Claim. (Cl. 47—60)

This discovery relates to a new and distinct variety of camellia plant, originating as a sport of the California Peoniaflora variety.

The blossoms of the parent variety are almost white, with a slight cream tint deep among the petals and an occasional bright pink (Phlox Pink, Plate 625/1) stripe, or in other instances a white ground color and scattered pin-head-size dots of bright pink.

This new variety, discovered by me on the parent plant grown in my nursery, is characterized as to novelty by the unique delicate yet rich coloring of the bloom. The base color, as disclosed in the accompanying drawing, is Dawn Pink and the occasional narrow stripes and the very numerous tiny spots are Phlox Pink. The whole flower appears to be irradiated by a delicate but distinct cream or yellow flush or glow, forming, with the other colors, a color combination entirely different from any other variety of camellia known to me.

Asexual reproduction through four generations shows these characteristics come true to form and are established.

In the accompanying drawing is illustrated a specimen of the flower and foliage as nearly as the same can be depicted as to the delicate coloring.

The following is a detailed description of the new variety, color terminology being in accordance with the Royal Horticultural Society Color Chart with exceptions noted from Ridgway's Color Standards and Nomenclature:

Parentage: Sport—California Peoniaflora variety.
Classification: Botanic—*Camellia japonica.*
Bud:
- *Size.*—Large.
- *Form.*—Globular.
- *Sepals.*—Smooth edge.
- *Calyx.*—Shape—apple. Size—large.

Bloom:
- *Size.*—When fully open, large; 4″ to 5″.
- *Borne.*—Singly to and on strong stem.
- *Form.*—Like very double rose bud, when first petal opens. Peony form, when fully opened.
- *Petalage.*—Double, 8 to 10 broad outer guard petals arranged regularly, and 75 to 100 irregular and narrower inner petals, forming a full peony-shaped flower.
- *Color.*—Base color—Dawn Pink, Plate 523/2, Chart 2; extreme highlights, Plate 523/1; stripes and spots, Phlox Pink, Plate 625/1, Chart 1.

Petals: Thick; inside and outside satiny; outer ones round or oval, and inner ones more slender, frequently indented at outer end.
- *Shape.*—Round; oval.
- *Arrangement.*—Irregular as above.
- *Lasting quality.*—On plant and as cut flower, long lasting.

Genital organs:
- *Stamens, anthers.*—Size—medium. Color—Chrome Yellow, Plate 605, vol. 2. Arrangement—scattered.
- *Stamens, filaments.*—Length—medium. Color—Pale Canary Yellow, Plate 3, vol. 1, page 2.
- *Pollen.*—Chrome Yellow, Plate 605, vol. 2, page 144.
- *Styles.*—Uneven; medium length. Color—Uranium Green, Plate 3, vol. 1, page 63.
- *Ovaries.*—Enclosed and slightly protruding.

Fruit: Occasionally bears a seed fruit, irregularly roundish, 1 to 8 seeds enclosed in outer shell or husk.
- *Aspect.*—Smooth.
- *Color at maturity.*—Auburn, Plate 2 (Ridgway).
- *Sepals.*—Soon falling; recurved.

Form of plant: Shrub growing into a small tree.
Growth: Vigorous; upright; branching.
Foliage:
- *Size.*—Large.
- *Quantity.*—Abundant.
- *Color.*—New foliage—Parsley Green, Plate 00962/1, vol. 2, page 193. Old foliage—Parsley Green, Plate 00962/1, vol. 2, page 193.
- *Shape.*—Oval pointed.
- *Texture.*—Upper side—glossy. Under side—smooth. Ribs and veins—ordinary.
- *Edge.*—Moderately serrated.

Wood:
- *New wood.*—Color—Cinnamon Brown, Plate 15 (Ridgway).
- *Old wood.*—Color—Cinnamon Brown, Plate 15 (Ridgway).

I claim:

A new and distinct variety of camellia plant, characterized as to novelty by the delicate yet rich coloring of the peony-shaped bloom, the base color of which is Dawn Pink, having occasional narrow stripes and very numerous tiny spots of Phlox Pink, the whole flower irradiated by a delicate but distinct cream or yellow flush or glow, substantially as shown and described.

ELVIN H. CARTER.